(12) United States Patent
Nikawa

(10) Patent No.: US 7,250,758 B2
(45) Date of Patent: Jul. 31, 2007

(54) INSPECTION METHOD AND APPARATUS USING SCANNING LASER SQUID MICROSCOPE

(75) Inventor: Kiyoshi Nikawa, Kanagawa (JP)

(73) Assignee: NEC Electronics Corporation, Kanagawa (JP)

(*) Notice: Subject to any disclaimer, the term of this patent is extended or adjusted under 35 U.S.C. 154(b) by 0 days.

(21) Appl. No.: 11/374,160

(22) Filed: Mar. 14, 2006

(65) Prior Publication Data
US 2007/0152664 A1 Jul. 5, 2007

(30) Foreign Application Priority Data
Mar. 15, 2005 (JP) ............................. 2005-073309

(51) Int. Cl.
*G01R 33/035* (2006.01)
(52) U.S. Cl. .................. 324/248; 324/501; 505/846
(58) Field of Classification Search ............... 324/244, 324/248, 501; 505/162, 845, 846
See application file for complete search history.

(56) References Cited

FOREIGN PATENT DOCUMENTS

JP 2002-313859 A 10/2002
JP 2004-93211 A 3/2004

*Primary Examiner*—Bot LeDynh
(74) *Attorney, Agent, or Firm*—Sughrue Mion, PLLC

(57) ABSTRACT

A non-destructive method of narrowing down the location of a failure in a sample includes a first step of acquiring first and second images of magnetic-field distributions obtained by scanning a laser beam irradiating first and second samples, respectively, and if there is a difference between the first and second images of the magnetic-field distributions, a second step of acquiring first and second current images from magnetic-field distributions acquired by scanning the first and second samples by a magnetic-field detector in a state in which a prescribed location on the first and second samples is being irradiated by the laser beam. The difference between the first and second current images is found and, based upon the difference image found, it becomes possible to identify a disparity in current paths relating to the prescribed location on the first and second samples.

16 Claims, 3 Drawing Sheets

INSPECTION METHOD AND APPARATUS USING SCANNING LASER SQUID MICROSCOPE

FIELD OF THE INVENTION

This invention relates to a non-destructive inspection apparatus and method. More particularly, the invention relates to an apparatus and method for narrowing down defect locations in a semiconductor device using a scanning laser SQUID (Superconducting Quantum Interference Device) microscope.

BACKGROUND OF THE INVENTION

Scanning laser SQUID microscopy is known as a method of non-destructive inspection of a sample such as a semiconductor wafer. With a scanning laser SQUID microscope, the area of a defect or a related location is irradiated with a laser. At such time a current flows, a magnetic field induced by the current is detected by a SQUID fluxmeter and an image is obtained by scanning either the laser or the sample (see Non-Patent Document 1). When a semiconductor substrate serving as the sample is irradiated with a laser beam, a pair consisting of an electron and positive hole generated by irradiation with the laser beam becomes an electric current owing to an electric field at a p-n junction, etc. This current is referred to as an OBIC (Optical Beam Induced Current). Alternatively, when heating occurs owing to irradiation with a laser beam, a temperature gradient produced by a defect or the like develops an imbalance and a current flows owing to the thermoelectric effect (see Non-Patent Document 1 and Patent Document 1).

It should be noted that Patent Document 2 discloses a non-destructive inspection apparatus for scanning a sample by moving the position on a sample that is irradiated with laser light, detecting a magnetic field, which is produced by scanning of the sample, using a SQUID fluxmeter, acquiring magnetic-field distribution data, subtracting the magnetic-field distribution data from standard distribution data or vice versa to thereby produce difference data, comparing the difference data with a positive first threshold value and a negative threshold value, determining that a defect of a first type exists at the laser-irradiated position when the difference data is greater than the first threshold value, and determining that a defect of a second type exists at the laser-irradiated position when the difference data is less than the second threshold value.

[Patent Document 1]

Japanese Patent Kokai Publication No. JP-P2002-313859A

[Patent Document 2]

Japanese Patent Kokai Publication JP-P2004-93211A

[Non-Patent Document 1]

K. Nikawa, S. Inoue, "Novel Nondestructive and Non-contact Failure Analysis and Process Monitoring Technique—Scanning Laser-SQUID Microscopy—", LSI Testing Symposium/2000 Conference (H12.11.9-10), pp. 203-208

[Non-Patent Document 2]

Bradley J. Roth, Nestor G. Sepulveda and John P. Wikswo, Jr., "Using a magnetometer to image a two-dimensional current distribution" J. Appl. Phys., 65(1), 1 Jan. 1989

SUMMARY OF THE DISCLOSURE

The image obtained by the inspection method that relies upon the conventional scanning laser SQUID microscope indicates the location at which a photoelectric current is produced, such as at a p-n junction, owing to laser irradiation. There are cases where this is not a location of a failure such as a short-circuit or break. With the conventional scanning method, therefore, it is difficult to narrow down the locations of failure except in special cases.

More specifically, as illustrated for example in Non-Patent Document 1, if a short-circuit occurs in a gate oxide film between polysilicon (a gate electrode) and an n-type diffusion layer and an OBIC current produced at an underlying p-n junction flows through the location of the short-circuit as part of a closed-circuit current path, then the location at which the failure occurred can be specified by the conventional inspection method relying upon a scanning laser SQUID microscope. However, with the conventional inspection method relying upon a scanning laser SQUID microscope, magnetic-field information that corresponds to the position of laser irradiation is displayed. Consequently, the field distribution image obtained is one that corresponds entirely to the source of photoelectric current generation and is not one that corresponds to a defect (failure) such as a wiring short-circuit or break that has occurred at a location remote from the position corresponding to the source of photoelectric current generation. As a result, it is extremely difficult to narrow down the location of a failure in a high precise manner based upon the image obtained by conventional scanning laser SQUID microscopy.

The present invention has been devised in view of the circumstances set forth above and its object is to solve the problems encountered in the prior art.

According to the present invention, a sample and the irradiating position of a laser beam are moved relative to each other to thereby scan the sample, a magnetic field is detected by a magnetic detector and the difference between an image of a magnetic-field distribution of the sample and that of a conforming article (or a known-good device) is detected. A location on the sample where a difference was observed in the image is irradiated with a laser beam, a magnetic-field distribution acquired by scanning the magnetic detector is converted to a current image and the difference between the current image of the sample and that of the conforming article is obtained. The location of a failure can be narrowed down based upon the difference image.

An inspection method in accordance with one aspect of the present invention, comprises the steps of:

executing processing with regard to first and second samples, which processing acquires a magnetic-field distribution by scanning the sample with a magnetic-field detector while a predetermined prescribed location on the sample is irradiated with a laser beam, and obtains a current image from the magnetic-field distribution; and finding a difference between the current images obtained with regard to respective ones of the first and second samples; thereby enabling identification of a disparity in current paths relating to the prescribed location with regard to the first and second samples based upon a difference image that represents the difference between the current images. In the present invention, if there is a difference between images of magnetic-field distributions obtained by scanning an irradiation position, at which the first and second samples are irradiated with the laser beam, relative to the first and second samples, then the prescribed location corresponds to a location at which the difference between the images of the magnetic-field distributions is confirmed.

Preferably, the method according to the present invention comprises the steps of:

(a) scanning each of first and second samples by moving each sample with a laser beam and a magnetic-field detector both being fixed relative the each sample, and acquiring respective magnetic-field distributions of the first and second samples by the magnetic-field detector;

(b) scanning the magnetic-field detector relative to the laser beam and each of the first and second samples, with a prescribed location on the each sample being irradiated fixedly by the laser beam, and acquiring respective magnetic-field distributions of the first and second samples by the magnetic-field detector, wherein the prescribed location on the each sample being irradiated fixedly by the laser beam corresponds to a location at which a difference is observed between the magnetic-field distributions of the first and second samples acquired in the step (a); and (c) obtaining respective current images from the magnetic-field distributions of the first and second samples acquired in the step (b) and finding a difference between the current images of the first and second samples; thereby enabling identification of a disparity in current paths relating to the prescribed location with regard to the first and second samples based upon a difference image that represents said difference between the current images.

An inspection apparatus in accordance with another aspect of the present invention, comprises: an irradiating unit for irradiating a sample with a laser beam; a magnetic-field detector; a scanning unit for scanning position of said magnetic-field detector relative to the sample to thereby scan the sample; a control unit for obtaining a current image from an image of a magnetic-field distribution acquired by scanning said magnetic-field detector in a state in which a prescribed location on the sample is being irradiated with the laser beam from said irradiating unit; and an output unit for outputting a difference image indicative of a difference between first and second current images, the first and second current images being obtained from images of magnetic-field distributions acquired by irradiating a prescribed location on respective ones of first and second samples with the laser beam from said irradiating unit and scanning said magnetic-field detector. In the present invention, it is determined from the difference image whether there is a disparity in current paths relating to the prescribed location on the first and second samples; and if such a disparity is exists, the location of the disparity is made identifiable.

Preferably, in the present invention, the apparatus further comprises scanning means for scanning the sample by moving the irradiation position of the laser beam relative to the sample. If there is a difference between images of magnetic-field distributions obtained by the scanning the first and second samples with the laser beam that irradiates the first and second samples, then the prescribed location is the location at which the difference is observed.

The meritorious effects of the present invention are summarized as follows.

In accordance with the present invention, it is possible to obtain an image that corresponds to the position of a defect such as a short-circuit or break, and it is possible to narrow down the location of failure non-destructively.

Still other features and advantages of the present invention will become readily apparent to those skilled in this art from the following detailed description in conjunction with the accompanying drawings wherein only the preferred embodiments of the invention are shown and described, simply by way of illustration of the best mode contemplated of carrying out this invention. As will be realized, the invention is capable of other and different embodiments, and its several details are capable of modifications in various obvious respects, all without departing from the invention. Accordingly, the drawing and description are to be regarded as illustrative in nature, and not as restrictive.

PREFERRED EMBODIMENTS OF THE INVENTION

A preferred embodiment of the present invention will now be described in detail with reference to the accompanying drawings.

Figure 1A:
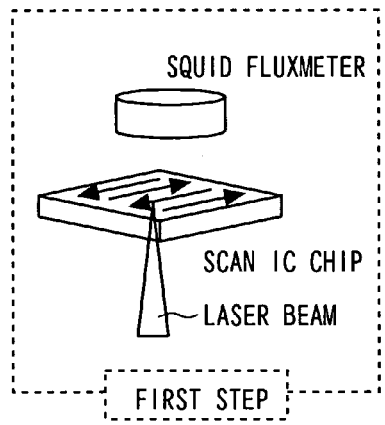
FIGS. 1A and 1B are diagrams useful in describing an embodiment of the present invention.
Figure 1B:
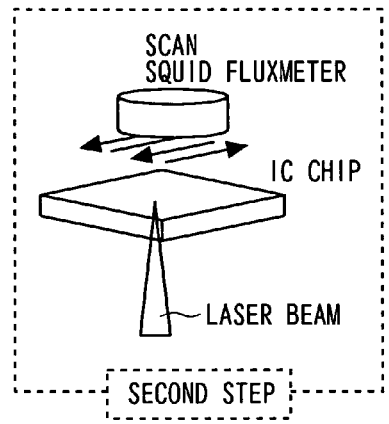

In the present invention, a sample to be inspected and the irradiation position of a laser beam are moved relative to each to scan the sample, a magnetic field is detected by a magnetic-field detector and a difference between images of magnetic-field distributions of the sample and a conforming article is obtained. A location on the sample and conforming article at which the difference between the magnetic-field distribution images is observed is irradiated with the laser beam and magnetic-field distributions are acquired by scanning the magnetic-field detector. The magnetic-field distributions acquired are converted to current images and the difference between the current image of the sample and the current image of the conforming article is found to make it possible to narrow down the location of the failure. FIGS. 1A and 1B are diagrams useful in describing an inspection method according to the present invention, and FIG. 2 is a diagram for describing the flow of processing of the inventive method.

In accordance with the present invention, first, as shown in FIG. 1A, an IC chip is irradiated from its back side with a laser beam. When a current such as an OBIC flows owing to the irradiation with the laser beam, a magnetic field is induced and the magnetic flux is detected by a SQUID fluxmeter disposed on the main side of the chip and constituting a magnetic-field detector. The laser beam is scanned across the back side of the IC chip (or the laser beam is held stationary and the IC chip is moved). The strength of the magnetic flux detected by the SQUID fluxmeter is correlated with information indicating the scanning position of the chip and is displayed on a display unit in the form of a grayscale (luminance) image, whereby a two-dimensional image that corresponds to the magnetic-field distribution can be obtained. The SQUID fluxmeter produces an output voltage that conforms to the strength of the magnetic field. A signal processor (or data processor) converts the output voltage of the SQUID fluxmeter to grayscale data of pixels corresponding to the position irradiated with the laser beam and displays the result on the display unit. Image data representing the magnetic-field distribution is obtained as a result.

The reason for irradiating the chip with the laser beam from the back side of the chip is to cause the laser beam to reach a p-n junction in the vicinity of the surface of the silicon substrate of the IC chip. On the main side of the IC chip the laser beam is reflected by a metal interconnection layer, etc., constituting the upper layer of the silicon substrate of the IC chip, and therefore the laser beam cannot reach the p-n junction in the vicinity of surface of the silicon substrate of the IC chip. In a case where inspection is performed using a wafer, it is preferred that the back side of the wafer be polished (finished) to a mirror surface.

Figure 2:
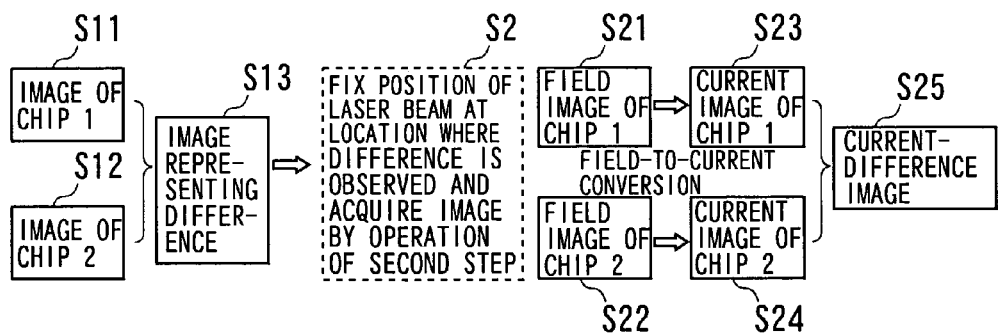
FIG. 2 is a diagram useful in describing the embodiment.

In accordance with the technique of a first step in FIG. 1A, the images of magnetic-field distributions of respective ones of an IC chip to be inspected and of a conforming IC chip (a known good device, also referred to as a "reference chip") are acquired (steps S11 and S12 in FIG. 2) and the difference between the images of the two magnetic-field distributions is acquired (step S13 in FIG. 2). A location at which the difference between flux strengths corresponds to the source of a photoelectric current is obtained from the difference image obtained. It may be so arranged that the image of the magnetic-field distribution of the reference chip is acquired in advance and stored in a storage device and, when this image is compared with the image of the magnetic-field distribution of the IC chip to be inspected, the stored image is read out of the storage device and the difference is found by an arithmetic unit or the image difference is displayed on the display unit.

Next, if a difference between the image of the IC chip to be inspected and the image of the reference chip is found from the difference image obtained at step S12 in FIG. 2, then, as illustrated in FIG. 1B, the laser beam is emitted while being held fixed and the SQUID fluxmeter is scanned across the surface of the sample (see step S2 in FIG. 2). That is, with regard to the IC chip to be inspected and the reference chip, the SQUID fluxmeter is scanned in the X and Y directions in a state in which irradiation is performed while the location irradiated by the laser beam is held stationary, and an image (magnetic-field image) of the magnetic-field distribution of the IC chip to be inspected and that of the reference chip are acquired (steps S21, S22 in FIG. 2). It goes without saying that it may be so arranged that the SQUID fluxmeter is held stationary instead of being scanned and the laser beam and sample are scanned simultaneously.

Next, the magnetic-field image of the IC chip to be inspected and of the reference chip are converted to images representing two-dimensional current distributions, the current distributions are obtained (steps S23 and S24 in FIG. 2) and the difference image between the two current distributions is obtained (step S25 in FIG. 2). If a failure such as a short-circuit or break exists in the difference image, then the failure is displayed at a position that corresponds to the location of the failure.

It should be noted that the same equipment may be used at the first and second steps in FIGS. 1A and 1B, or the equipment used at the first step and the equipment used at the second step may be different. For example, the SQUID fluxmeter used in the first step may be large in size to raise the accuracy of field detection, and the SQUID fluxmeter used in the second step may be small in size. A small-size SQUID fluxmeter is not only effective in obtaining a high spatial resolution but is also advantageous in that the scanning mechanism can be reduced in size and weight.

Figure 3A:
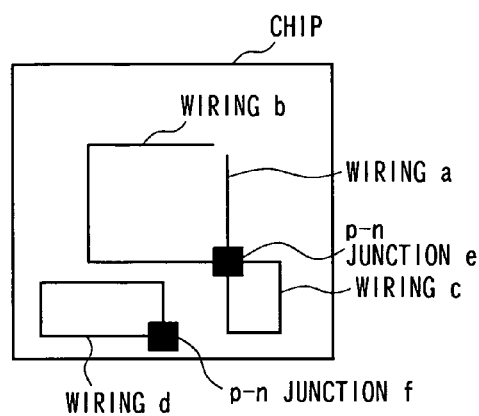
FIGS. 3A and 3B are diagrams useful in describing the embodiment.

FIGS. 3A to 5C are schematic views useful in describing an embodiment of a process for narrowing down failure location on a IC chip according to the present invention. As shown in FIG. 3A, it is assumed that a chip (a conforming or known good chip) has a p-n junction e to which are connected one ends of wirings a and b, and that the chip has no short circuit between the other ends of the wirings a and b. On the other hand, as shown in FIG. 3B, it is assumed that a chip (a defective chip) has a p-n junction e to which are connected one ends of wirings a and b, and that the chip has a short-circuit defect between the other ends of the wirings a and b.

Figure 3B:
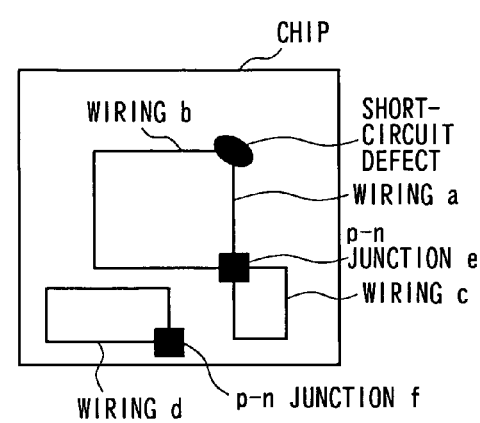
Figure 4A:
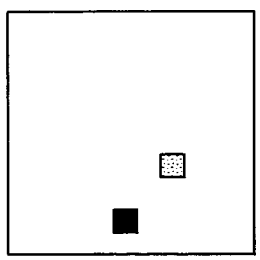
FIGS. 4A, 4B and 4C are diagrams useful in describing the embodiment.
Figure 4B:
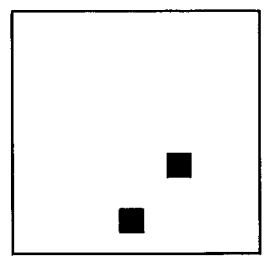

FIG. 4A illustrates the image (image data) of a magnetic-field distribution obtained at the first step (scanning by the laser beam) of FIG. 1A in relation to the chip of FIG. 3A. FIG. 4B illustrates the image (image data) of a magnetic-field distribution obtained at the first step (scanning by the laser beam) in relation to the chip of FIG. 3B. Although there is no particular limitation, the images shown in FIGS. 4A and 4B are such that the strength of the magnetic flux is made to correspond to a grayscale; the higher the strength of the magnetic flux, the darker the tone of the grayscale.

In the case of the good chip of FIG. 3A, the current produced by irradiating the p-n junction e with the laser beam flows through wiring c connected to the p-n junction e and forming a closed path. Current produced by irradiating a p-n junction f with the laser beam flows through wiring d connected to the p-n junction f and forming a closed path. Since the ends of the wirings a and b opposite the ends connected to the p-n junction e are not short-circuited (i.e., since these ends are open), wirings a and b do not form a current loop.

On the other hand, in the case of the defective chip of FIG. 3B, a short-circuit defect exists between the wirings a and b connected to the p-n junction 3. Consequently, the current produced by irradiating the p-n junction e with the laser beam flows through a closed path comprising the p-n junction e and wirings a and b, and wiring c connected to the p-n junction e and forming a closed path. Current produced by irradiating the p-n junction f with the laser beam flows through the wiring d connected to the p-n junction f and forming a closed path.

In the case of the chip shown in FIG. 3A, the magnetic field from the single closed path c in relation to the p-n junction e is detected by the SQUID fluxmeter (see FIG. 4A). In the case of the chip shown in FIG. 3B, the combined magnetic fields from the two closed paths in relation to the p-n junction e are detected by the SQUID detector (see FIG. 4B).

Figure 4C:
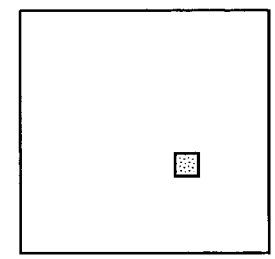

When the difference image between the magnetic-field distribution images of FIGS. 4A and 4B is found, FIG. 4C is obtained. It may be so arranged that a difference is found for every value of magnetic field corresponding to the position irradiated by the laser beam, or it may be so arranged that image processing is executed for every item of pixel data to obtain the difference image. It will be understood from the difference image of FIG. 4C that between the chip of FIG. 3A and the chip of FIG. 3B there is a disparity in the magnetic fields corresponding to the p-n junction e. On the other hand, the magnetic-field distributions corresponding to the p-n junction f are the same in the chip of FIG. 3A and the chip of FIG. 3B and, as a result, there is no display by a grayscale signal (luminance signal) at the position corresponding to the p-n junction f in the difference image of FIG. 4C. It goes without saying that it may be so arranged that if the value of the difference (or absolute value of the difference) exceeds a prescribed threshold value in the course of processing for obtaining the difference image of FIG. 4C, then the fact that there is such a difference is indicated.

As mentioned above, the location at which there is a difference between the chips of FIGS. 3A and 3B in the difference image of FIG. 4C is a location, such as a p-n junction, where a photoelectric current is produced; it is not necessarily the location of a failure such as a short-circuit or break. That is, as mentioned above, the location of a failure cannot be specified solely from the image of FIG. 4C except in special cases.

Figure 5A:
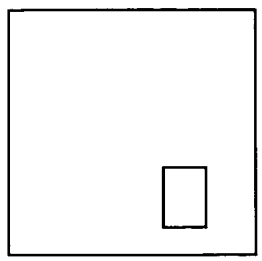
FIGS. 5A, 5B and 5C are diagrams useful in describing the embodiment.
Figure 5B:
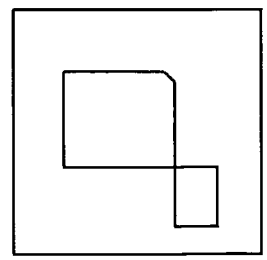

Accordingly, in this embodiment, with regard to each of the chips of FIGS. 3A and 3B, the p-n junction e in the substrate surface of the chip is irradiated with the stationary laser beam from the back side of the chip, the SQUID fluxmeter is caused to scan on the main side of the chip, a conversion using the Fourier transform is applied to the image (two-dimensional data) of the magnetic-field distribution of the chip obtained by the scan, and an image of two-dimensional current values is obtained. With regard to the method of obtaining the current distribution by applying the conversion using the Fourier transform, refer to Non-Patent Document 2, by way of example. FIGS. 5A and 5B are the current images of the IC chips of FIGS. 3A and 3B, respectively, thus obtained.

Figure 5C:
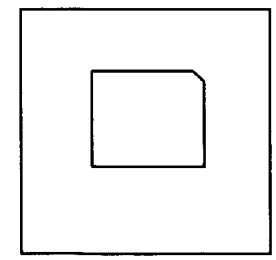

If the difference between the current images of FIGS. 5A and 5B is found by image processing, a difference image of the kind shown in FIG. 5C is obtained. As illustrated in FIG. 5C, the current loop ascribable to the short-circuit defect of wirings a and b is output and displayed on the display unit as an image constituting the current image. That is, the current-difference image of FIG. 5C indicates the disparity in the current paths of the chips of FIGS. 3A and 3B. In the case of the short-circuit defect, part of the difference image of the current path of FIG. 5C is the location of the short-circuit defect. With the good chip of FIG. 3A, the mutually opposing ends of the wirings a and b are open and therefore it is possible to ascertain from the difference image of FIG. 5C that the mutually opposing ends of the wirings a and b of the chip shown in FIG. 3B are short-circuited. It goes without saying that it may be so arranged that if the value of the difference (or absolute value of the difference) exceeds a prescribed threshold value in the course of processing for obtaining the current-difference image of FIG. 5C, then the fact that there is such a difference is indicated.

The description above has been rendered taking a short-circuit defect as an example. However, the location of a failure can be specified from a difference image between current images in a similar manner also in the case of a break defect. For example, assume that the good chip is the one in which the mutually opposing ends of the wirings a and b are connected together, as in FIG. 3B, and that the chip of FIG. 3A is one having a break defect (namely a defect in which the wirings a and b have become disconnected). In this case, FIG. 5B becomes the current image of the good chip and FIG. 5A the current image of the defective chip. If the difference between these two current images is found, the current-difference image of FIG. 5C is obtained. It can be ascertained that the current loop illustrated in FIG. 5C has not been formed in the defective chip, i.e., that there is a break in the current loop.

Thus, in accordance with the present invention, it is possible to narrow down the location of a physical failure such as a short-circuit or break in a chip. This has been extremely difficult with the conventional inspection methods. That is, it has been verified that the present invention is applicable to fault analysis of semiconductor devices, such as identification of failures such as short-circuits and disconnections.

Figure 6A:
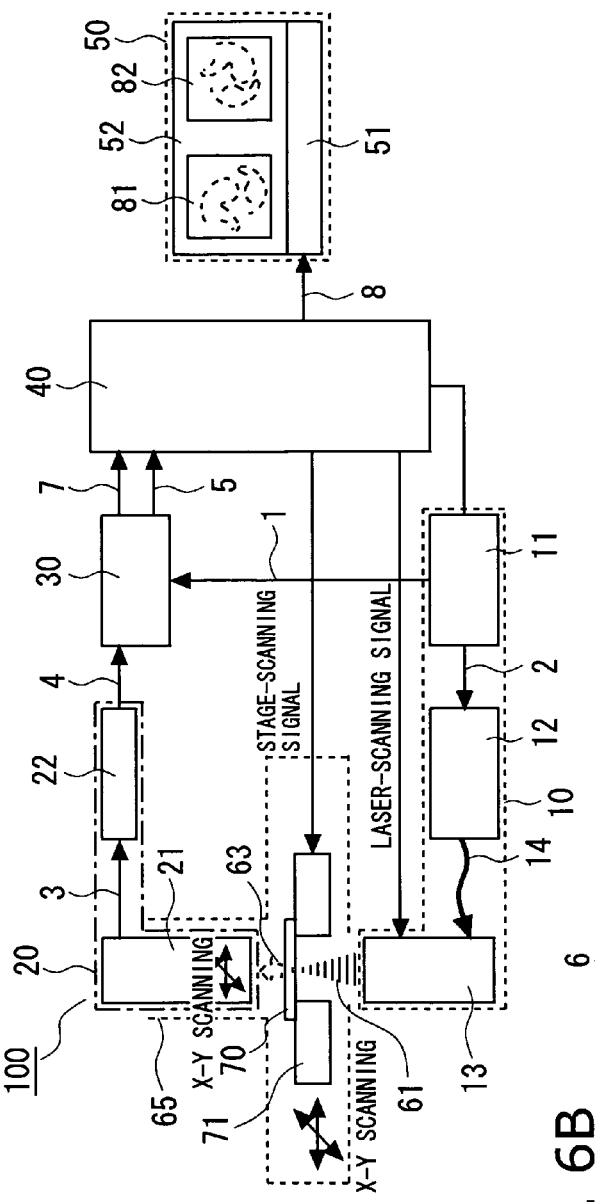
FIGS. 6A and 6B are diagrams illustrating the structure of an apparatus according to the embodiment.
Figure 6B:
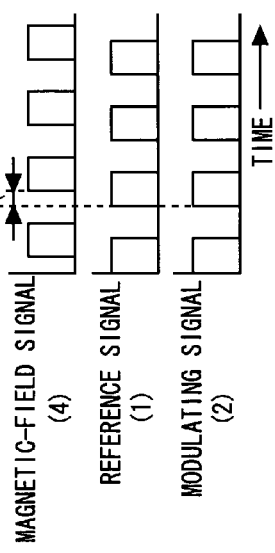

FIG. 6A is a diagram illustrating an embodiment of the structure of an inspection apparatus for practicing the present invention. FIG. 6B is a diagram useful in describing an example of the timing waveforms of a reference signal 1, modulating signal 2 and magnetic-field signal 4. With reference to FIG. 6A, the inspection apparatus comprises a modulated-beam generator 10 for producing modulated light, which is intensity-modulated by the modulating signal 2 synchronized to the prescribed reference signal 1, and generating a modulated beam 61 by causing the light to converge; a sample table 71 on which a sample 70 is placed and moved in such a manner that a prescribed irradiation position on the sample will be irradiated with the modulated beam 61; a magnetic-field detector 20 for detecting a magnetic field (magnetic flux), which is induced by a current produced when the sample 70 is irradiated with the modulated beam 61, and outputting the magnetic-field signal 4; a signal extracting unit 30 for extracting the intensity of the magnetic field and a phase difference 6 (see FIG. 6B) between the reference signal 1 and the magnetic-field signal 4 and outputting these as an intensity signal 5 and a phase-difference signal 7, respectively; a controller 40 for controlling irradiation of the sample 70 with the modulated beam 61 and controlling positioning of the sample table 71 in accordance with information representing the irradiation position, receiving the intensity signal 5 and phase-difference signal 7 as inputs and outputting these in correlation with the irradiation position information, and executing processing to subject the image of the magnetic-field distribution to a conversion using the Fourier transform and acquire a current signal; and a display unit 50, to which at least one of the intensity signal 5 and phase-difference signal 7 is input together with the irradiation position information, for displaying an image.

The modulated-beam generator 10 includes a pulse generator 11 for generating and outputting the reference signal 1 and the modulating signal 2 (see FIG. 6B) synchronized to the reference signal 1; a laser beam generator 12, which is constituted by a fiber laser, etc., equipped with a modulating mechanism, for generating modulated light (laser beam) that is intensity-modulated by the modulating signal 2 output from the pulse generator 11; an optical fiber 14 for guiding the laser light; and an optical unit 13 for generating the modulated beam 61 by converging the light guided by the optical fiber 14.

The magnetic-field detector 20 has a SQUID fluxmeter 21 and an electronic circuit (also referred to as a "SQUID electronic circuit") 22 for generating the magnetic-field signal 4 from the output signal (voltage output) 3 of the SQUID fluxmeter 21 and outputting the magnetic-field signal 4. By way of example, the SQUID fluxmeter 21 employs a high-temperature superconducting SDQUID fluxmeter. The electronic circuit 22 is capable of using an FLL (Flux-Locked Loop) circuit.

The signal extracting unit 30 comprises, e.g., a 2-phase lock-in amplifier (not shown), although this does not constitute a particular limitation. The magnetic-field signal 4 from the electronic circuit 22 and the reference signal 1 from the pulse generator 11 are input to the signal extracting unit 30, which proceeds to extract from the magnetic-field signal 4 a frequency component identical with that of the reference signal 1 and to output the intensity signal 5 and the phase-difference signal 7 that conforms to the phase difference 6 (see FIG. 6B) between the magnetic-field signal 4 and the reference signal 1.

The controller 40 controls the position of the sample table 71 (sample 70) by, e.g., a stage scanning signal, controls the optical unit 13 of the modulated-beam generator 10 by the laser scanning signal as necessary and irradiates the sample 70 while scanning the modulated beam 61 across the sample 70 at the first step in FIG. 1A. On the other hand, at the second step of FIG. 1B, it may be so arranged that the sample table 71 and optical unit 13 are held stationary, the position irradiated by the modulated beam 61 is positioned at a prescribed location on the sample 70, this position is irradiated with the stationary beam and the SQUID fluxmeter 21 is made to scan in the X and Y directions by a SQUID-fluxmeter scanning signal (not shown) from the controller 40. Alternatively, it may be so arranged that the SQUID fluxmeter 21 is held stationary, the position irradiated by the modulated beam 61 is positioned at a prescribed location on the sample 70 and the sample table 71 and optical unit 13 are scanned in unison in the X and Y directions to thereby scan the magnetic field detected by the SQUID fluxmeter 21.

Further, the controller 40 accepts the intensity signal 5 and phase-difference signal 7 from the signal extracting unit 30 and exercises control for displaying a scanning laser SQUID microscopic image in sync with scanning of the stage and laser-beam irradiation position or in sync with scanning of the SQUID fluxmeter. In the case of scanning of the laser at the first step in FIG. 1A, the controller 40 outputs an image display signal 8 by combining the information indicating the irradiation position of the modulated beam 61 and the intensity signal 5 or phase-difference signal 7 corresponding to this irradiation position information. In the case of scanning of the SQUID fluxmeter at the second step in FIG. 1B, the controller 40 outputs the image display signal 8 for displaying a current distribution obtained in conformity with a combination of information indicating the position of the SQUID fluxmeter and intensity signal 5 or phase-difference signal 7 corresponding to this position information.

The display unit 50, which is equipped with a personal computer 51 and monitor 52, receives the image display signal 8 from the controller 40 and outputs an intensity image 81 of the magnetic-field signal 4 corresponding to the magnetic field at the laser-beam scanning position (first step) or a phase-difference image 82 corresponding to the phase difference between the magnetic-field signal 4 and the reference signal 1. Alternatively, the display unit 50 outputs the intensity image 81 or phase-difference image 82 corresponding to the magnetic field at the scanning position (second step) of the SQUID fluxmeter. It should be noted that in the description rendered above with regard to FIGS. 3 to 5, the image of the magnetic-field distribution is illustrated as one type in order to simplify the description. However, it is preferred that the intensity image 81 and phase-difference image 82 be used, as illustrated in FIG. 6A.

Next, an example of operation of the apparatus according to the embodiment shown in FIG. 6 will be described. In this embodiment, an IC chip and a silicon wafer, etc., are used as the sample 70. It goes without saying that the sample may be a compound semiconductor wafer or FTF substrate, etc. The sample 70 is placed on the sample table 71, the reference signal 1 and modulating signal 2 synchronized thereto are generated by the pulse generator 11, the reference signal 1 is output to the signal extracting unit 30, the modulating signal 2 is output to the laser beam generator 12 constituted by a fiber laser (of wavelength 1065 nm, by way of example) incorporating a modulating function, an intensity-modulated laser beam is generated, the beam is guided to the optical unit 13 by the optical fiber 14 and the modulated laser beam is narrowed down on the sample 70.

The modulated beam 61 irradiates the initial irradiation point, the magnetism from the sample 70 is detected by the SQUID fluxmeter 21 and the detected field is output from the electronic circuit 22 as the magnetic-field signal 4. The latter is input to the signal extracting unit 30, which outputs the intensity signal 5 and the phase-difference signal 7 to the controller 40.

The controller 40 correlates the intensity signal 5 and phase-difference signal 7 with the position irradiated with the modulated beam 61 and outputs these signals to the personal computer 51 as the image display signal 8. The personal computer 51 stores the intensity signal 5 and phase-difference signal 7 in the storage unit of the personal computer 51.

X-Y scanning of the sample table 71 by the stage scanning signal is combined as necessary with scanning of the modulated beam 61 by the laser scanning signal, each of the irradiation points in the desired area of the sample 70 to be inspected are selected successively, the modulated beam 61 is emitted and processing for storing the intensity signal 5 and phase-difference signal 7 in the storage unit of the personal computer 51 as the image display signal 8 in correlation with information indicative of the position of the irradiation point is executed.

The personal computer 51 presents a grayscale (or luminance) display conforming to the intensity signal 5 or phase-difference signal 7 on the monitor 52 (a color display may be presented if desired). At the first step in FIG. 1A, the personal computer 51 presents a display in correlation with the laser irradiation point on the sample 70, as illustrated in FIGS. 4A and 4B. In this case, it may be so arranged that one of the intensity image 81 corresponding to the intensity signal 5 and phase-difference image 82 corresponding to the phase-difference signal 7 is displayed. An arrangement in which the image of the magnetic field is displayed in real time in correlation with the scanning point may be adopted. It is permissible to adopt an arrangement in which tone (luminance) conforming to the intensity signal 5 and phase-difference signal 7 at each scanning position of one sample is stored beforehand in correspondence with the scanning position, and a grayscale (luminance) image conforming to the intensity signal 5 and phase-difference signal 7 stored in the storage unit in correspondence with the scanning position is displayed on the monitor 52 upon completion of the entire scan of one sample or off-line at any time thereafter. It goes without saying that the output unit is not limited to a monitor and that the output may be sent to a printer or file device.

In this embodiment, the frequency of the modulating signal 2 can be set to any value up to a maximum of, e.g., 1 MHz by using a fiber laser equipped with a modulating mechanism as the laser beam generator 12. In the selection of the frequency of the modulated signal, it is necessary to select a frequency having little noise if the magnetic-field signal is very weak and the S/N (signal-to-noise) ratio is poor. Further, if the frequency dependence of the signal representing the magnetic field induced by the photoelectric current ascribable to irradiation with the modulated beam (this signal shall be referred to as a "laser-induced field signal") is large, then the S/N ratio may be improved by selecting a frequency for which the laser-induced field signal becomes large. In a case where the frequency dependence of the laser-induced field signal differs greatly depending upon the location of the sample 70, it is necessary to select several modulation frequencies. In this embodiment, laser light having a wavelength of 1065 nm is used and therefore if the sample 70 is a silicon wafer, the wafer can be irradiated from the back side thereof with the laser beam, the beam can pass through the silicon wafer and the modulated beam can reach the p-n junction in the vicinity of the surface of the silicon wafer. The back surface of the silicon wafer preferably is polished to a mirror surface. The modulated beam 61 applied from the back side of the silicon wafer can be made to reach the p-n junction efficiently.

It is possible to use an HTS (High-Temperature Superconducting) SQUID as the SQUID fluxmeter 21 and a very small flux density B of less than 1 pT can be detected. The SQUID fluxmeter 21 is equipped with a shield 65. The SQUID fluxmeter usually detects magnetic flux in a direction perpendicular to the sample 70.

Since the magnetic-field signal 4 that is output from the electronic circuit 22 usually contains noise, only the frequency component identical with the modulation frequency is extracted by the 2-phase lock-in amplifier (signal extracting unit 30), thereby improving the S/N ratio. By using the 2-phase lock-in amplifier as the signal extracting unit 30, not only is solely a frequency component identical with the frequency of the reference signal 1 that is output from the pulse generator 11 extracted but it is also possible to separate and output the phase-difference signal 7 indicative of the phase difference between this component and the reference signal 1 as well as the intensity signal 5. By making the size of the chip 6 mm×10 mm, for example, narrowing down the beam diameter of the modulated beam 61 to 10 μm and scanning the sample table 71, which is constituted by a ceramic stage, in the X-Y directions, a magnetic-field distribution image is obtained. The modulation frequency is assumed to be 100 KHz, by way of example. The intensity image 81 and phase-difference image 82 of the chip are obtained.

At the second step in FIG. 1B, the position on the sample 70 irradiated with the modulated beam 61 is held stationary (the location corresponding to the p-n junction e in FIGS. 3A and 3B is held fixed and irradiated) and the SQUID fluxmeter 21 is caused to scan across the sample 70 to acquire the magnetic-field distribution. In this case the SQUID fluxmeter 21 may be moved in the X and Y directions in accordance with the control signal from the controller 40. Alternatively, it may be so arranged that the SQUID fluxmeter 21 is held stationary, the irradiation position of the modulated beam 61 is fixed on the sample 70 and the sample 70 and irradiation position of the modulated beam 61 are moved in unison in the X and Y directions under these conditions. In the second step also the signal extracting unit 30 that receives the magnetic-field signal 4 from the electronic circuit 22 outputs the intensity signal 5 and phase-difference signal 7 and the controller 40 stores the intensity signal 5 and phase-difference signal 7 in correlation with the scanning position. Upon completion of the scanning of one sample, two-dimensional current-distribution data is obtained by applying a conversion using a Fourier transform to the two-dimensional data of the magnetic-field distribution that has been stored in memory in correspondence with the scanning position. The display unit 50 displays the image of the current distribution as a grayscale image on the monitor 52 in correlation with the scanning position of the SQUID fluxmeter 21.

It should be noted that the structure shown in FIG. 6A has been described in accordance with an example in which the intensity signal and the phase-difference signal indicating the phase difference between the magnetic-field signal and the reference signal are output separately from the magnetic-field signal by the magnetic-field detector. As a matter of course, however, the invention is also applicable to an arrangement in which only the intensity signal is output.

As many apparently widely different embodiments of the present invention can be made without departing from the spirit and scope thereof, it is to be understood that the invention is not limited to the specific embodiments thereof except as defined in the appended claims.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

What is claimed is:

1. An inspection method comprising the steps of:
   (a) scanning each of first and second samples by moving each sample with a laser beam and a magnetic-field detector both being fixed relative the each sample, and acquiring respective magnetic-field distributions of the first and second samples by the magnetic-field detector;
   (b) scanning the magnetic-field detector, with respect to the laser beam and each of the first and second samples, with a prescribed location on the each sample being irradiated fixedly by the laser beam, and acquiring respective magnetic-field distributions of the first and second samples by the magnetic-field detector, wherein the prescribed location on the each sample being irradiated fixedly by the laser beam corresponds to a location at which a difference is observed between the magnetic-field distributions of the first and second samples acquired in the step (a); and
   (c) obtaining respective current images from the magnetic-field distributions of the first and second samples acquired in the step (b) and finding a difference between the current images of the first and second samples; thereby enabling identification of a disparity in current paths relating to the prescribed location with regard to the first and second samples based upon a difference image that represents said difference between the current images.

2. An inspection method comprising the steps of:
   (A) executing processing with regard to first and second samples, said processing acquiring a magnetic-field distribution by scanning each sample with a magnetic-field detector while a predetermined prescribed location on the sample is irradiated with a laser beam, and obtaining a current image from the magnetic-field distribution; and
   (B) finding a difference between the current images obtained with regard to respective ones of the first and second samples;
   thereby enabling identification of a disparity in current paths relating to the prescribed location with regard to the first and second samples based upon a difference image that represents said difference between the current images.

3. The method according to claim 2, wherein if there is a difference between images of magnetic-field distributions, obtained by scanning an irradiation position, at which each of the first and second samples is irradiated with the laser beam, relative to each of the first and second samples, then said prescribed location corresponds to a location at which the difference between the images of the magnetic-field distributions is confirmed.

4. The method according to claim 2, further comprising the steps of:

in advance of processing of the step (A), moving the first sample and the irradiation position of the laser beam relative to each other to thereby scan the first sample, and acquiring a first magnetic-field distribution by the magnetic-field detector;

in advance of processing of the step (A), moving the second sample and the irradiation position of the laser beam relative to each other to thereby scan the second sample, and acquiring a second magnetic-field distribution by the magnetic-field detector;

if there is a difference between the first magnetic-field distribution obtained with regard to the first sample and the second magnetic-field distribution obtained with regard to the second sample, adopting the location at which this difference is observed as the prescribed location, executing the processing of the step (A) and, when executing said processing, irradiating said prescribed location fixedly with the laser beam and scanning the magnetic-field detector, thereby acquiring an image of a third magnetic-field distribution and an image of a fourth magnetic-field distribution;

as processing of the step (B), converting the images of the third and fourth magnetic-field distributions obtained with regard to the first and second samples, respectively, to first and second current images, respectively;

as processing of the step (B), finding the difference between the first and second current images obtained with regard to the first and second samples, respectively; and as processing of the step (B), determining from a difference image between the first and second current images whether there is a disparity in current paths relating to the fixed irradiation location of the laser beam on the first and second samples, and if such a disparity exists, enabling identification of the location of the disparity.

5. The method according to claim 2, wherein one of the first and second samples is a sample to be inspected and the other of the first and second samples is a conforming sample serving as a reference;

whereby it is possible to narrow down location of a failure in the sample to be inspected.

6. The method according to claim 2, further comprising the steps of:

using a modulated beam as the laser beam, said modulated beam being obtained by generating intensity-modulated light that is intensity-modulated based upon a modulating signal synchronized to a reference signal, and causing the modulated light to converge on the sample;

on the basis of a magnetic-field signal detected by the magnetic-field detector and the reference signal, deriving magnetic-field intensity and phase difference between the magnetic-field signal and the reference signal and outputting these as an intensity signal and phase-difference signal, respectively; and displaying the intensity signal and/or phase-difference signal in correlation with information indicative of scanning position.

7. The method according to claim 2, wherein the magnetic-field detector includes a SQUID fluxmeter.

8. An inspection apparatus comprising:

an irradiating unit for irradiating a sample with a laser beam;

a magnetic-field detector;

a scanning unit for scanning position of said magnetic-field detector relative to the sample to thereby scan the sample;

a control unit for obtaining a current image from an image of a magnetic-field distribution acquired by scanning said magnetic-field detector in a state in which a prescribed location on the sample is being irradiated with the laser beam from said irradiating unit; and an output unit for outputting a difference image indicative of a difference between first and second current images, the first and second current images being obtained from images of magnetic-field distributions acquired by irradiating a prescribed location on respective ones of first and second samples with the laser beam from said irradiating unit and scanning said magnetic-field detector.

9. The apparatus according to claim 8, wherein it is determined from the difference image output from said output unit whether there is a disparity in current paths relating to the prescribed location on the first and second samples; and if such a disparity is exists, the location of the disparity is made identifiable.

10. The apparatus according to claim 8, wherein said output unit outputs, in the form of an image, the disparity in the current paths relating to the prescribed location on the first and second samples.

11. The apparatus according to claim 8, further comprising a scanning unit for scanning the sample by moving the irradiation position of the laser beam relative to the sample;

wherein if there is a difference between images of magnetic-field distributions obtained by the scanning the first and second samples with the laser beam that irradiates the first and second samples, then the prescribed location is the location at which the difference is observed.

12. The apparatus according to claim 8, wherein said scanning unit scans the sample by moving the irradiation position of the laser beam relative to the sample, the position of said magnetic-field detector at such time being held stationary relative to the sample;

said magnetic-field detector detects a magnetic field induced by current that flows through the sample owing to irradiation with the laser light, in a state in which said detector is held stationary relative to the sample;

if, with regards to said first and second samples scanned by the laser beam, there is a difference between images of magnetic-field distributions obtained by said magnetic-field detector held stationary relative to each of the said first and second samples, said control unit converts the images of the magnetic-field distributions, which have been acquired by moving the position of said magnetic-field detector relative to the each sample by said scanning unit to thereby scan the sample, while fixedly irradiating each of the first and second samples by said irradiating unit adopting a location at which the difference between the images of the magnetic-field distributions is observed as the prescribed location, to current images, thereby obtaining first and second current images to find the difference between the first and second current images; and said output unit outputs the difference between the first and second current images;

wherein it is determined whether there is a disparity in current paths relating to the irradiation location of the laser beam on the first and second samples and, if such a disparity is exists, enabling identification of the location of the disparity.

13. The apparatus according to claim 8, further comprising:
- a modulated beam generating unit for emitting a modulated beam as the laser beam, said modulated beam being obtained by generating modulated light that is intensity-modulated based upon a modulating signal synchronized to a reference signal, and causing the modulated beam to converge; and
- a signal extracting unit for deriving magnetic-field intensity and phase difference between the magnetic-field signal and the reference signal, on the basis of a magnetic-field signal detected by said magnetic-field detector and the reference signal to output an intensity signal and phase-difference signal, respectively;
- said output unit displaying the intensity signal and/or phase-difference signal in correlation with information indicative of scanning position.

14. The apparatus according to claim 8, wherein one of the first and second samples is a sample to be inspected and the other of the first and second samples is a conforming sample serving as a reference;
- whereby it is possible to narrow down location of a failure in the sample to be inspected.

15. The apparatus according to claim 8, wherein said magnetic-field detector includes a SQUID fluxmeter.

16. The apparatus according to claim 8, wherein each of the first and second samples is scanned by moving each sample with said laser beam and said magnetic-field detector both being fixed relative to the each sample, and respective magnetic-field distributions of the first and second samples are acquired by the magnetic-field detector;

the magnetic-field detector is scanned, with respect to the laser beam and each of the first and second samples, while a prescribed location on the each sample is being irradiated fixedly by the laser beam, in which the prescribed location on the each sample being irradiated fixedly by the laser beam corresponds to a location at which a difference is observed between the magnetic-field distributions of the first and second samples acquired, and respective magnetic-field distributions of the first and second samples are acquired by the magnetic-field detector; and wherein respective current images from the magnetic-field distributions of the first and second samples are acquired and a difference is found between the current images of the first and second samples; thereby enabling identification of a disparity in current paths relating to the prescribed location with regard to the first and second samples based upon a difference image that represents said difference between the current images.

* * * * *